(12) United States Patent
Imanishi et al.

(10) Patent No.: US 8,263,956 B2
(45) Date of Patent: Sep. 11, 2012

(54) OPTICAL FLOW CHANNEL MEASURING INSTRUMENT

(75) Inventors: Shingo Imanishi, Kanagawa (JP); Motohiro Furuki, Tokyo (JP)

(73) Assignee: Sony Corporation, Tokyo (JP)

( * ) Notice: Subject to any disclaimer, the term of this patent is extended or adjusted under 35 U.S.C. 154(b) by 549 days.

(21) Appl. No.: 12/472,760

(22) Filed: May 27, 2009

(65) Prior Publication Data
US 2009/0294702 A1    Dec. 3, 2009

(30) Foreign Application Priority Data

May 29, 2008  (JP) ................. 2008-141042
Jan. 7, 2009   (JP) ................. 2009-001233

(51) Int. Cl.
*G01N 21/49*   (2006.01)
*G01N 21/85*   (2006.01)
*G01N 21/00*   (2006.01)

(52) U.S. Cl. ........ 250/576; 356/436; 356/440; 356/441; 356/442

(58) Field of Classification Search .......... 250/574, 250/576; 356/73, 432, 436, 440–442; 359/838–884
See application file for complete search history.

(56) References Cited

U.S. PATENT DOCUMENTS

| | | | |
|---|---|---|---|
| 5,159,397 A * | 10/1992 | Kosaka et al. | 356/73 |
| 6,115,119 A * | 9/2000 | Sieracki et al. | 356/337 |
| 6,175,750 B1 | 1/2001 | Cook et al. | |
| 2005/0030519 A1 | 2/2005 | Roth | |
| 2006/0073076 A1 | 4/2006 | Ichiki et al. | |
| 2006/0181791 A1 | 8/2006 | Van Beek et al. | |
| 2007/0195318 A1 * | 8/2007 | Yamamoto | 356/300 |

FOREIGN PATENT DOCUMENTS

| | | |
|---|---|---|
| JP | 04-270961 | 9/1992 |
| JP | 05-346390 | 12/1993 |
| JP | 06-043090 | 2/1994 |
| JP | 2002-540391 | 11/2002 |
| JP | 2003-107099 | 4/2003 |
| JP | 2004-85323 | 3/2004 |
| JP | 2007-500529 | 1/2007 |
| JP | 2007-501394 | 1/2007 |
| WO | 2008-035336 | 3/2008 |

OTHER PUBLICATIONS

Japanese Office Action for corresponding JP2009-001233 issued on Mar. 23, 2010.

* cited by examiner

*Primary Examiner* — Georgia Y Epps
*Assistant Examiner* — Renee Naphas
(74) *Attorney, Agent, or Firm* — K&L Gates LLP

(57) ABSTRACT

An optical measuring instrument includes: a flow channel for allowing a specimen to be circulated therein; a first light source including a light emitting diode for emitting light to be used for optical adjustment and/or image confirmation in the flow channel; a second light source for irradiating light upon the specimen circulated in the flow channel; and a light detector for detecting the spectrum intensity of the light emitted from the first and second light sources.

8 Claims, 7 Drawing Sheets

OPTICAL FLOW CHANNEL MEASURING INSTRUMENT

CROSS REFERENCES TO RELATED APPLICATIONS

The present application claims priority to Japanese Priority Patent Application JP 2008-141042 filed in the Japan Patent Office on May 29, 2008. and Japanese Priority Patent Application JP 2009-001233 filed in the Japan Patent Office on Jan. 7, 2009. the entire contents of which are hereby incorporated by reference.

BACKGROUND

This application relates to an optical measuring instrument for optically detecting a specimen using a flow channel. More particularly, the present application relates to an optical measuring instrument for optically detecting a specimen which circulates in a flow channel, a wavelength calibration method for a light detector for use with an optical measuring instrument and an optical measuring method which uses a wavelength calibration method.

In recent years, together with the development of the analysis method, a method has been and is being developed wherein organic fine particles such as cells and microorganisms or fine particles such as micro beads are circulated in a flow channel and, during such circulation, the fine particles are measured individually and the measured fine particles are analyzed or sorted. Technical improvement of the analysis method called flow cytometry as a representative example of such a method of analysis or dispensing of fine particles using a flow channel is progressing rapidly.

The flow cytometry is an analysis method wherein fine particles of an object of analysis are fed into fluid to form a train of the fine particles and a laser beam or the like is irradiated upon the lined up fine particles to detect fluorescent light or scattered light generated from the fine particles to analyze the fine particles and further carry out sorting of the fine particles based on a result of the analysis.

Since an apparatus which carries out the flow cytometry is disadvantageous in that it is large in size and low in general-purpose properties, a method which uses a microchip wherein a fine flow channel is formed in a substrate made of an inorganic material such as silicon or glass or a high-molecular material such as plastics has been proposed in recent years.

For example, a fine particle sorting microchip has been proposed and disclosed in Japanese Patent Laid-Open No. 2003-107099 (hereinafter referred to as Patent Document 1). The fine particle sorting microchip disclosed in Patent Document 1 includes a substrate and several elements provided on the substrate and at least including an introduction flow channel for introducing solution containing fine particles, a sheath flow forming flow channel disposed at least on one side of the introduction flow channel, a fine particle measuring part for measuring the fine particles introduced thereto, two or more fine particle sorting flow channels disposed on the downstream with respect to the file particle measuring parts for sorting and recovering the fine particles, and two or more electrodes located in the proximity of flow channel ports from the fine particle measuring parts to the fine particle sorting flow channels for controlling the moving direction of the fine particles.

Meanwhile, a cell analyzing and separating apparatus has been proposed and is disclosed in Japanese Patent Laid-Open No. 2004-85323 (hereinafter referred to as Patent Document 2). The cell analyzing and separating apparatus disclosed in Patent Document 2 includes a flow channel into which fluid containing a specimen to be introduced in laminar flows into a specimen sorting section is introduced, a pair of flow channels disposed symmetrically on the opposite sides of the flow channel for allowing only the fluid to be introduced thereinto, means for introducing external force into the specimen sorting section only when the observation specimen is to be discharged from the specimen sorting section, a specimen recovering flow channel disposed on the downstream side of the flow channel into which the specimen is introduced so that the fluid containing the specimen from which only the selected specimen is recovered in laminar flows from the specimen sorting section, and a pair of fluid paths disposed symmetrically on the opposite sides of the specimen recovering flow channel for receiving the unnecessary specimen discharged thereinto.

Incidentally, wavelength calibration of a light detector used in optical measurement in which a flow channel is used is generally carried out such that a light source which emits light of a bright line spectrum is used to irradiate the light in advance on a flow channel before a specimen is circulated in the flow channel and the light is measured by the light detector to carry out the wavelength calibration.

SUMMARY

As described above, wavelength calibration of a light detector in optical measurement wherein a flow channel is used is usually carried out using a light source which emits light of a bright line spectrum.

However, in the case of an apparatus which uses a light source, which emits light of a bright line spectrum, for illumination, it sometimes requires a large condenser lens or a heat radiation countermeasure and has a tendency that the size thereof increases.

Further, where a detector whose spectrum resolution is approximately 10 nm or more is used, very small optical axis adjustment does not allow detection of a spectrum shift but sometimes makes wavelength calibration rather difficult.

Further, a light source which emits light of a bright line spectrum has a problem that it is difficult to irradiate flashlight upon a flow channel.

Therefore, it is desirable to provide a novel technique which uses a flow channel and can easily carry out wavelength calibration of a light detector to be used while achieving miniaturization of an apparatus to be used.

Investigations have been made about the light source to be used and recognition of a light source capable of irradiating light having a spectrum width in accordance with an embodiment of the present application.

According to an embodiment, there is provided an optical measuring instrument including a flow channel for allowing a specimen to be circulated therein, a first light source including a light emitting diode for emitting light to be used for optical adjustment and/or image confirmation in the flow channel, a second light source for irradiating light upon the specimen circulated in the flow channel, and a light detector for detecting the spectrum intensity of the light emitted from the first and second light sources.

The optical measuring instrument may further include wavelength calibration means for carrying out wavelength calibration of the light detector based on the spectrum intensity, detected by the light detector, of the light emitted from the first light source.

In this instance, although the particular wavelength calibration method carried out by the wavelength calibration means is not limited particularly, as an example, the wavelength calibration means may compare a spectrum intensity distribution, detected by the light detector, of the light emitted from the light source with a spectrum intensity distribution determined in advance of the light emitting diode to carry out the wavelength calibration of the light detector.

The optical measuring instrument may further include image confirmation means for carrying out image conformation in the flow channel based on optical information generated through the flow channel by irradiating the light upon the flow channel using the first light source.

In this instance, although the particular image confirmation method carried out by the image confirmation means is not limited particularly, as a example, the first light source may carry out flashlight irradiation in synchronism with the circulation of the specimen, and the image confirmation means may confirm the state of the specimen through an image based on the optical information generated from the specimen upon the flashlight irradiation.

The optical measuring instrument may further include light synthesis means for synthesizing the light emitted from the first light source and the light emitted from the second light source.

In this instance, although the particular configuration used for the light synthesis means is not limited particularly, for example, the light synthesis means may include a dichroic mirror or a beam splitter.

The optical measuring instrument may further include light separation means for separating the light transmitted through the flow channel to light to the light detector and light to the image confirmation means.

In this instance, although the particular configuration used for the light separation means is not limited particularly, as an example, the light separation means may include a ring-shaped mirror.

Although the type of the light emitting diode which can be used in the optical measuring instrument described above is not limited particularly, preferably the light emitting diode exhibits a spectrum intensity distribution having a spectrum width of 100 nm or more.

In the optical measuring instrument, a light source formed from a light emitting diode is used in place of a related light source, which emits light of a bright line spectrum, for wavelength calibration of a light detector. Therefore, miniaturization of the instrument can be anticipated, and wavelength calibration of the light detector can be calculated readily.

According to another embodiment, there is provided a wavelength calibration method for a light detector, including a light irradiation step of irradiating light of a light emitting diode upon a flow channel, a spectrum intensity acquisition step of acquiring a spectrum intensity of the light emitted through the flow channel at the light irradiation step, and a wavelength calibration step of calibrating a detection wavelength of a light detector based on the spectrum intensity distribution acquired at the spectrum intensity acquisition step.

Although the wavelength calibration method carried out at the wavelength calibration step is not limited particularly, for example, a method of comparing a spectrum intensity distribution acquired at the spectrum intensity acquisition step and a spectrum intensity distribution of the light emitting diode determined in advance with each other to calibrate the detection wavelength of the light detector can be used.

Although the type of the light emitting diode which can be used in the wavelength calibration method described above is not limited particularly, preferably the light emitting diode exhibits a spectrum intensity distribution having a spectrum width of 100 nm or more.

According to a further embodiment, there is provided an optical measuring method including a first light irradiation step of irradiating light of a light emitting diode upon a flow channel, a spectrum intensity acquisition step of acquiring a spectrum intensity of the light emitted through the flow channel at the first light irradiation step, a wavelength calibration step of calibrating a detection wavelength of a light detector based on the spectrum intensity distribution acquired at the spectrum intensity acquisition step, a circulation step of circulating a specimen in the flow channel, a second light irradiation step of irradiating light upon the specimen, and an optical information detection step of detecting optical information from the specimen by means of the light detector.

Although the wavelength calibration method carried out at the wavelength calibration step is not limited particularly, for example, a method of comparing a spectrum intensity distribution acquired at the spectrum intensity acquisition step and a spectrum intensity distribution of the light emitting diode determined in advance with each other to calibrate the detection wavelength of the light detector can be used.

The optical measuring method may further include a third light irradiation step of irradiating the light of the light emitting diode on the flow channel in which the specimen is circulated.

In this instance, the optical measuring method may further include an image confirmation step of carrying out image conformation in the flow channel based on optical information generated through the flow channel at the third light irradiation step.

Although the particular image confirmation method carried out at the image confirmation step is not limited particularly, as an example, at the third light irradiation step, flashlight irradiation may be carried out in synchronism with the circulation of the specimen, and at the image confirmation step, the state of the specimen may be confirmed based on the optical information generated from the specimen upon the flashlight irradiation.

The optical measuring method may further include a position adjustment step of carrying out position adjustment of the light detector or an image confirmation means for carrying out the image confirmation based on optical information generated through the flow channel at the first light irradiation step and/or the third light irradiation step.

In this instance, the optical measuring method may further include a light synthesis step of synthesizing the light emitted at the first light irradiation step and/or the third light irradiation step and the light emitted at the second light irradiation step.

In this instance, although the particular light synthesis method at the light synthesis step is not limited particularly, the light synthesis may be carried out using a dichroic mirror or a beam splitter.

The optical measuring method may further include a light separation step of separating the light transmitted through the flow channel to light to the light detector and light to the image confirmation means.

In this instance, although the particular light separation method at the light separation step is not limited particularly, for example, the light separation may be carried out using a ring-shaped mirror.

Although the type of the light emitting diode which can be used in the optical measuring method described above is not limited particularly, preferably the light emitting diode exhibits a spectrum intensity distribution having a spectrum width of 100 nm or more.

Here, a technical term used herein is defined. The term "specimen" is defined as any substance which can be circulated in the flow channel including cells and microorganisms, fine particles relating to living organisms such as liposome, DNA and protein, synthetic particles such as latex particles, gel particles and particles for industrial use and so forth.

Additional features and advantages are described in, and will be apparent from, the following Detailed Description and the figures.

DETAILED DESCRIPTION

Figure 1:
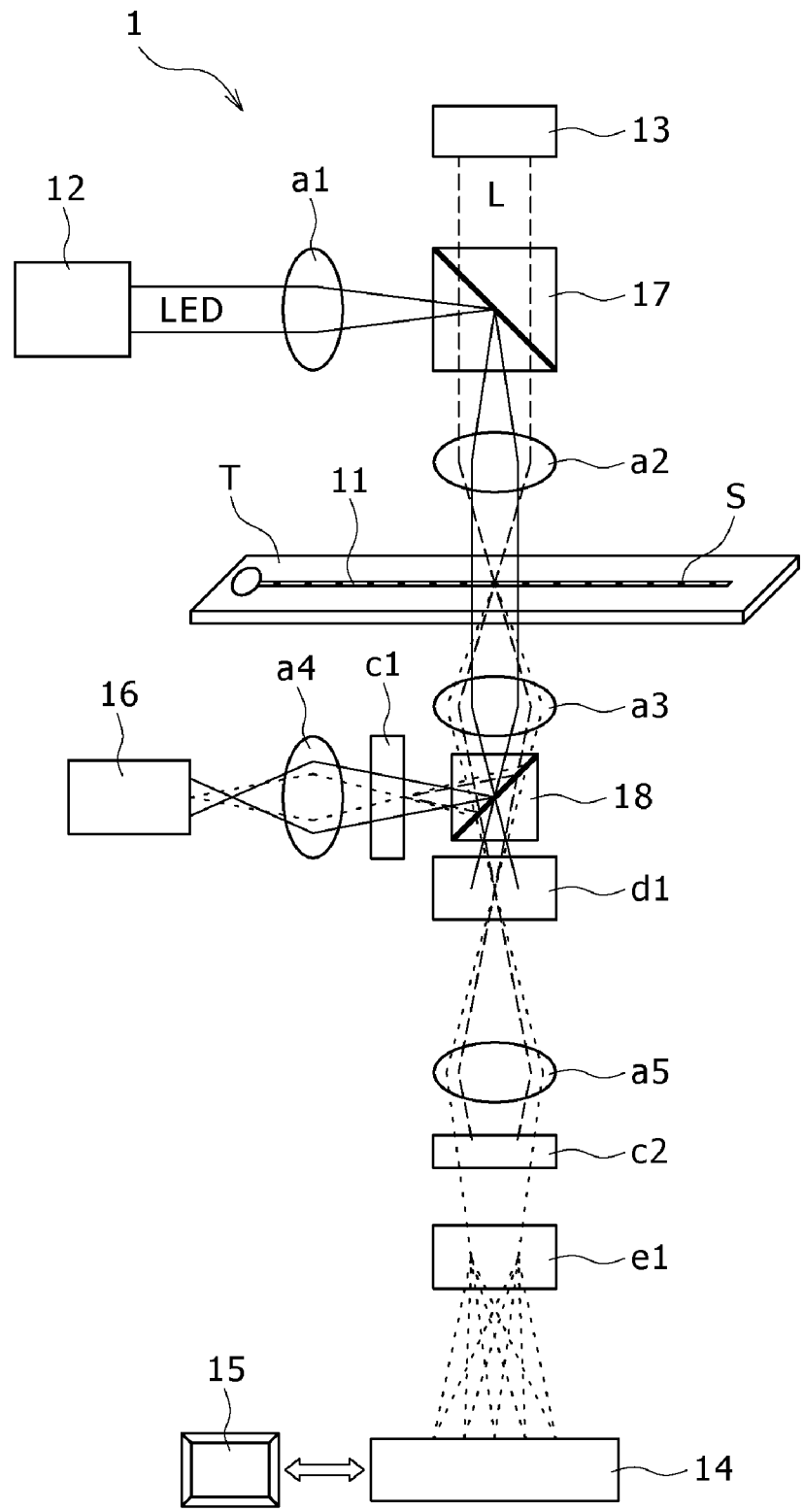
FIG. 1 is a schematic view showing an optical measuring instrument according to an embodiment.

The present application will be described below in greater detail in accordance with an embodiment.
1. Optical measuring instrument
1-1. Flow channel 11
1-2. First light source 12
1-3. Second light source 13
1-4. Light detector 14
1-5. Wavelength calibration section 15
1-6. Image confirmation section 16
1-7. Light synthesis section 17
1-8. Light separation section 18
2. Wavelength calibration method
2-1. Light irradiation step 101 (first light irradiation step in the optical measuring method)
2-2. Spectrum intensity acquisition step 102
2-3. Wavelength calibration step 103
3. Optical measuring method
3-1. Circulation step 104
3-2. Second light irradiation step 105
3-3. Optical information detection step 106
3-4. Third light irradiation step 107
3-5. Image confirmation step 108
3-6. Position adjustment step 109
3-7. Sorting method
3-8. Light synthesis step 110
3-9. Light separation step 111
3-10. Flow of the optical measuring method 100
<1. Optical Measuring Instrument>

FIG. 1 schematically shows an optical measuring instrument 1 according to an embodiment.

Referring to FIG. 1, the optical measuring instrument 1 shown includes a flow channel 11, a first light source 12, a second light source 13, and a light detector 14. As occasion demands, the optical measuring instrument 1 may further include a wavelength calibration section 15, an image confirmation section 16, a light synthesis section 17 and a light separation section 18. The components mentioned are individually described in detail.

1-1. Flow Channel 11

A specimen S is circulated in the flow channel 11, and light is irradiated from the first light source 12 and the second light source 13 hereinafter described at a predetermined location of the flow channel 11 to carry out detection of various kinds of optical information.

The form of the flow channel 11 which can be used in the optical measuring instrument 1 is not limited particularly, and the flow channel 11 can be designed freely. For example, the flow channel 11 is not limited to such a two-dimensional or three-dimensional flow channel 11 formed on a substrate T of plastics, glass or the like as shown in FIG. 1, but also such a flow channel 11 which is used in a related flow cytometer can be used in the optical measuring instrument 1.

Also the flow channel width, flow channel depth and flow channel sectional shape of the flow channel 11 are not limited particularly but can be designed freely only if the flow channel can produce laminar flows. For example, also for a micro flow channel having a flow channel width of 1 mm or less, the optical measuring instrument 1 can be used. Particularly, if a micro flow channel having a flow channel width equal to or greater than 10 μm but equal to or smaller than 1 mm is used, then an optical measuring method according to an embodiment hereinafter described can be carried out preferably.

It is to be noted that, where the flow channel 11 formed on the substrate T is adopted, preferably the bottom of the flow channel 11 is formed from a transparent material. This is because this makes it possible to dispose the light detector 14 hereinafter described on the opposite side to the first light source 12 and the second light source 13 with respect to the substrate T so that optical information from the bottom side of the flow channel 11 can be detected.

1-2. First Light Source 12

The first light source 12 is formed from a light emitting diode (LED) for allowing optical adjustment and/or image confirmation in the flow channel 11. More particularly, LED light is irradiated from the first light source 12 toward the flow channel 11, and based on optical information generated through the flow channel 11, wavelength calibration or position adjustment of the light detector 14, position adjustment of the image confirmation section 16, optical adjustment such as position adjustment and so forth between the second light source 13 or a condensing lens a2 hereinafter described and the flow channel 11 and image confirmation in the flow channel 11 using the image confirmation section 16 are carried out.

Although the type of the LED which can be used in the optical measuring instrument 1 is not limited particularly, preferably an LED of a spectrum intensity distribution having a spectrum width of 100 nm or more is used. This is because, if an LED whose spectrum width is 100 nm or more is used, then optical axis adjustment after the light emitted from the LED is spectralized by the light detector 14 can be carried out easily. A white-light LED is an example of the LED of a spectrum intensity distribution having a spectrum width of 100 nm or more.

Preferably, an LED having a known spectrum intensity distribution is used. This is because, if an LED having a known spectrum intensity distribution is used, then wavelength calibration of the light detector 14 can be carried out readily.

In the optical measuring instrument 1, since a light source formed from an LED is used in order to carry out optical adjustment and/or image confirmation in the flow channel 11, miniaturization of the optical measuring instrument 1 can be implemented without the necessity to use a condenser lens.

Further, since the LED emits a small amount of heat, there is no necessity to take measures such as a countermeasure for heat radiation. Also this contributes to implementation of miniaturization of the optical measuring instrument 1.

Further, where the LED is used, confirmation of the light condensing position of the second light source 13 and image confirmation and optical adjustment by the image confirmation section 16 can be carried out over a wide visual field.

In addition, since the spectrum of the LED exhibits not a bright line spectrum but a broad distribution, even where the resolution of the light detector 14 is low, a spectrum shift by very small optical axis adjustment can be detected to carry out wavelength calibration of the light detector 14.

1-3. Second Light Source 13

The second light source 13 irradiates light upon the specimen S circulated in the flow channel 11 to obtain optical information from the specimen S using the light detector 14.

Although the type of the light to be irradiated from the second light source 13 is not limited particularly, in order to allow fluorescent light or scattered light to be generated with certainty from the specimen S, light whose direction, wavelength and intensity are fixed is preferably used. As an example, a laser or an LED can be used. Where a laser is used, although the type of the laser is not limited particularly, one, two or more of an argon ion (Ar) laser, a helium-neon (He—Ne) laser, a dye laser and a krypton (Kr) laser may be freely used solely or in combination.

1-4. Light Detector 14

The light detector 14 detects the spectrum intensity of light emitted from the first light source 12 and the second light source 13. More particularly, the light detector 14 detects the spectrum intensity of light emitted through the flow channel 11 when the first light source 12 is used to irradiate light upon the flow channel 11, and detects the spectrum intensity of light emitted from the specimen S when the second light source 13 is used to irradiate light upon the specimen S circulated along the flow channel 11.

The type of the light detector 14 which can be used in the optical measuring instrument 1 is not limited particularly only if the light detector 14 can detect the spectrum intensity of light, and known light detectors can be selectively used. For example, one, two or more of a fluorescent light measuring instrument, a scattered light measuring instrument, a transmission light measuring instrument, a reflection light measuring instrument, a diffraction light measuring instrument, an ultraviolet spectrometer, an infrared spectrometer, a Raman spectrometer, an FRET measuring instrument, a FISH measuring instrument, various other spectrometers, a multichannel light detector formed from a plurality of light detectors juxtaposed in an array and so forth can be freely used solely or in combination.

Figure 2:
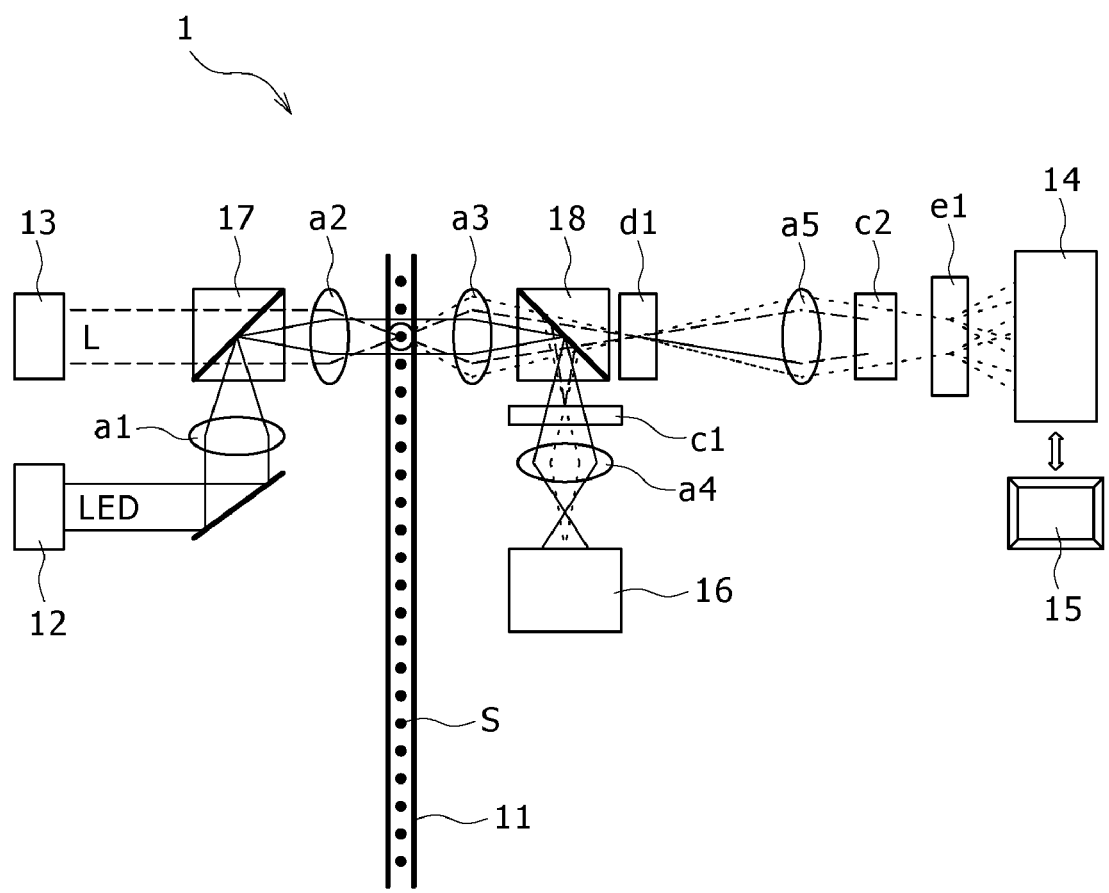
FIG. 2 is a schematic view showing an optical measuring instrument according to another embodiment.

Although the arrangement location of the light detector 14 in the optical measuring instrument 1 is not limited particularly only if the spectrum intensity of light emitted from the first light source 12 and the second light source 13 can be detected, preferably the light detector 14 is arranged on the opposite side to the first light source 12 and the second light source 13 with respect to the flow channel 11 as seen in FIGS. 1 and 2. Where the light detector 14 is arranged on the opposite side to the first light source 12 and the second light source 13 with respect to the flow channel 11, the first light source 12 and the second light source 13 can be arranged with a higher degree of freedom.

Further, since the space for the light detector 14 needs not be assured adjacent the first light source 12 and the second light source 13, also it is possible to increase the number of such first light sources 12 or second light sources 13. On the contrary, on the light detector 14 side, since there is no necessity to assure the space for any light source, also it is possible to arrange a plurality of light detectors 14 to carry out various kinds of measurement at the same time.

1-5. Wavelength Calibration Section 15

The wavelength calibration section 15 is means for carrying out wavelength calibration of the light detector 14 based on the spectrum density, detected by the light detector 14, of light generated from the first light source 12.

Figure 3A:
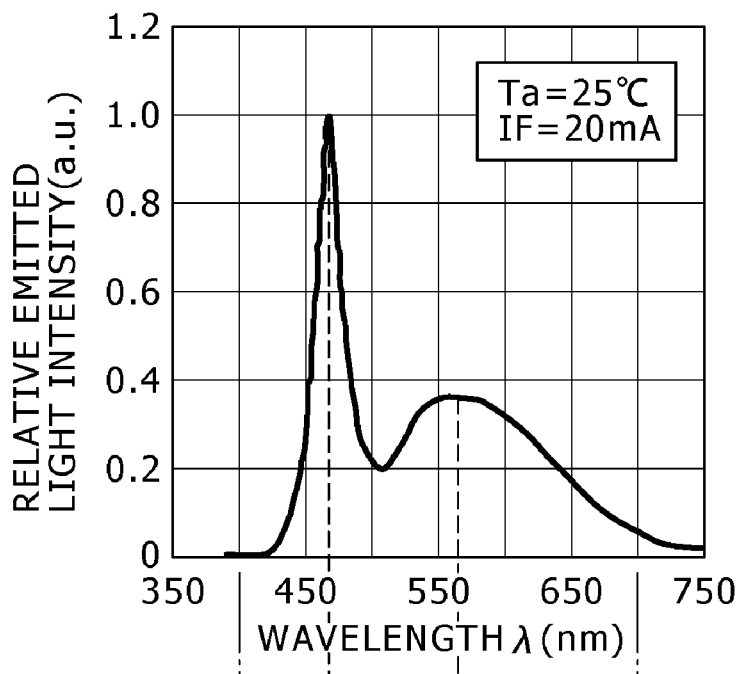
FIGS. 3A and 3B are graphs illustrating a method of comparing a spectrum intensity distribution of a known LED and a spectrum intensity distribution of measured light with each other as an example of a particular wavelength calibration method carried out by a wavelength calibration section and a wavelength calibration method.
Figure 3B:
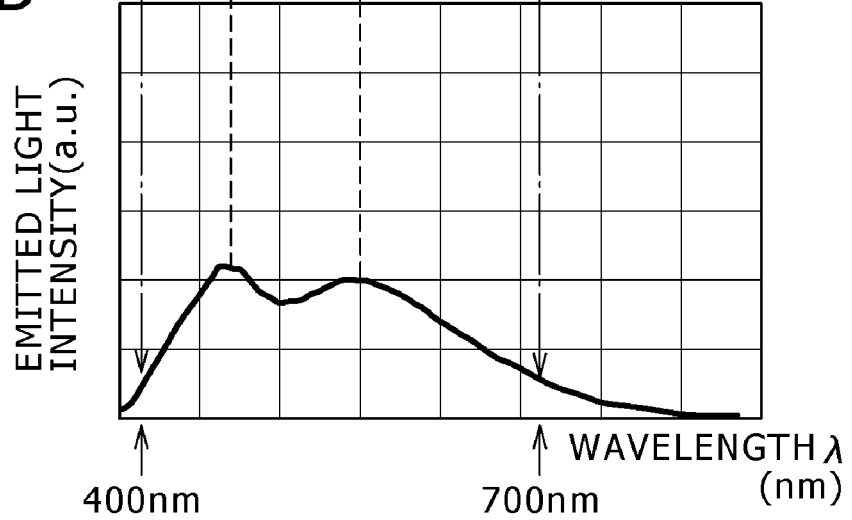

Although the particular wavelength calibration method carried out by the wavelength calibration section 15 is not limited particularly, it is possible to adopt a method of carrying out wavelength calibration of the light detector 14 by comparing the spectrum intensity distribution (refer to FIG. 3B), detected by the light detector 14, of light emitted from the first light source 12 and the spectrum intensity distribution (refer to FIG. 3A), determined in advance, of LED light same as that emitted from the first light source 12 with each other.

1-6. Image Confirmation Section 16

Although the image confirmation section 16 is not means essentially required by the optical measuring instrument 1, it carries out image confirmation in the flow channel 11 based on optical information generated through the flow channel 11 when light is irradiated upon the flow channel 11 using the first light source 12.

Where a light source which emits light of a bright line spectrum is used as in the related optical measurement to carry out image confirmation, since the wavelength band is wide, chromatic aberration correction for an image formation lens is required, and there is a problem that the size of the optical measuring instrument itself increases. However, with the optical measuring instrument 1 according to an embodiment, since an LED is used for the first light source, the wavelength band can be suppressed to a very small bandwidth in comparison with the related light source. Therefore, the optical measuring instrument 1 provides such an advantage that the necessity for chromatic aberration correction for an image formation lens is eliminated and a compact optical system can be constructed.

The type of the image confirmation section 16 which can be used in the optical measuring instrument 1 is not limited particularly only if it can carry out image confirmation in the flow channel 11, and known devices can be selectively used freely. For example, a detector which uses an area image pickup element such as a charge coupled device (CCD) element, a complementary metal oxide semiconductor (CMOS) device or the like can be used as the image confirmation section 16.

Although the particular image confirmation method carried out by the image confirmation section 16 is not limited particularly, as an example, a method can be used wherein the first light source 12 is used to emit flashlight in synchronism with circulation of the specimen S to confirm a state of the specimen S such as the position, speed, shape or color through an image based on optical information generated from the specimen S.

Further, the image confirmation section 16 not only can confirm a state of the specimen S circulated in the flow channel 11 through an image but also can be used before the specimen S is circulated in the flow channel 11 in order to carry out optical adjustment such as wavelength calibration or position adjustment of the light detector 14, position adjustment of the image confirmation section 16 and position adjustment of the second light source 13 or the condensing lens a2 with respect to the flow channel 11 based on optical information generated through the flow channel 11 when LED light is irradiated from the first light source 12 toward the flow channel 11.

1-7. Light Synthesis Section 17

The light synthesis section 17 is means for synthesizing light emitted from the first light source 12 and light emitted from the second light source 13. Although the light synthesis section 17 is not essentially required by the optical measuring instrument 1, where the light synthesis section 17 is provided, the following advantage can be achieved.

Since the optical measuring instrument 1 includes the two light sources, that is, the first light source 12 and the second light source 13, where light beams are irradiated upon the same position of the flow channel 11, at least one of the light beams is irradiated in an oblique direction upon the flow channel 11. Where light is irradiated in an oblique direction upon the flow channel 11, scattering or reflection of the light sometimes occurs, and this may have an influence on spectrum intensity detection of light or image detection. Therefore, it is a possible idea to synthesize two beams of light emitted from the two light sources, that is, the first light source 12 and the second light source 13, such that a resulting light beam is irradiated in a perpendicular direction upon the flow channel 11.

However, where a light source which emits light of a bright line spectrum and an excitation laser light source are used as in the related optical measurement, that one of bright line spectrum light wavelengths which overlaps with the wavelength of the excitation light cannot be used for the light synthesis, resulting in possibility that the utilization efficient of the light amount may drop.

On the other hand, in the optical measuring instrument 1, since an LED is used as the first light source, synthesis with the excitation light such as laser light is possible, and the influence of scattering or reflection of light upon spectrum intensity detection or image detection of light can be reduced. As a result, effective optical measurement with a high degree of accuracy can be anticipated.

Further, since the LED light emitted from the first light source 12 and the excitation light emitted from the second light source 13 are synthesized and the synthesized light is irradiated in a perpendicular direction upon the flow channel 11, also the advantage that the visual field of the monitor image becomes bright and the visual observability is improved in image confirmation by the image confirmation section 16 is provided.

Further, if the wavelength of the LED light emitted from the first light source 12 is set sufficiently long in comparison with the wavelength of the excitation light emitted from the second light source 13, then the two wavelengths can be synthesized efficiently by the light synthesis section 17. As a result, also the advantage that the utilization efficiency of both of the LED light amount and the excitation light amount is raised can be achieved.

The type of the light synthesis section 17 which can be used in the optical measuring instrument 1 is not limited particularly only if the light synthesis section 17 can be used to synthesize the light emitted from the first light source 12 and the light emitted from the second light source 13, and known devices can be selectively used freely. For example, a dichroic mirror or a beam splitter can be used as the light synthesis section 17.

1-8. Light Separation Section 18

The light separation section 18 is means for separating light transmitted through the flow channel 11 into light to the light detector 14 and light to the image confirmation section 16. Light formed by synthesis of light emitted from both of the first light source 12 and the second light source 13 by the light synthesis section 17 and transmitted through the same location of the flow channel 11 needs be separated into light to the light detector 14 and light to the image confirmation section 16.

Figure 4:
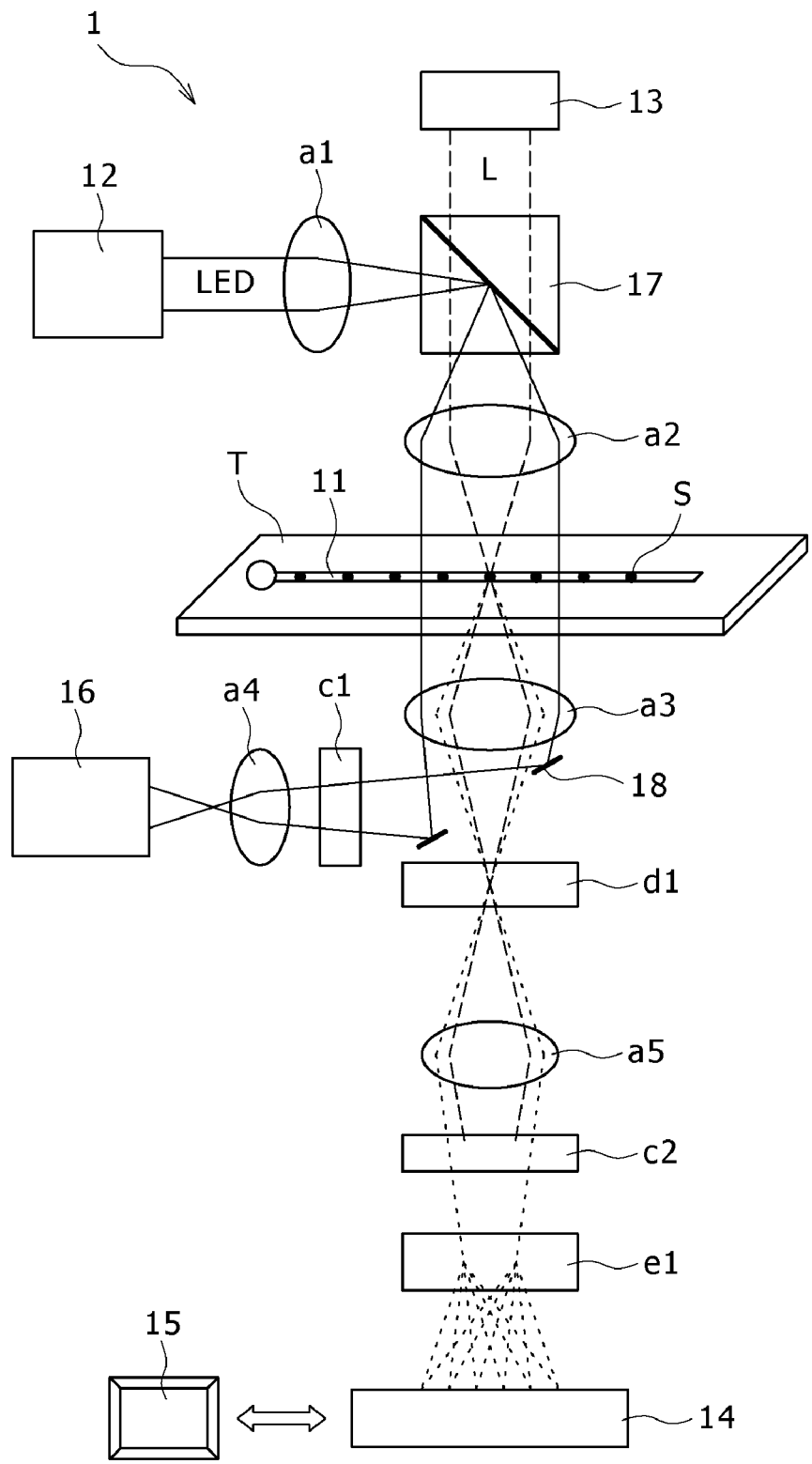
FIG. 4 is a schematic view showing an optical measuring instrument according to a further embodiment.

The type of the light separation section 18 which can be used in the optical measuring instrument 1 is not limited particularly only if it can separate light transmitted through the flow channel 11 into light to the light detector 14 and light to the image confirmation section 16, and known devices can be selectively used freely. For example, a beam splitter or a ring-shaped mirror can be used.

Where a beam splitter is used, for example, if AR coating (Anti Reflection Coating) is applied only to one face, then light of a predetermined amount can be separated into light to the light detector 14 and light to the image confirmation section 16. In the optical measuring instrument 1, if the ratio of the light separation is set to 3 to 5% to the image confirmation section 16, then the light can be used sufficiently for image confirmation of the arrangement of the flow channel 11 or the manner in the flow channel 11.

Where the image confirmation section 16 is used for position adjustment of the flow channel 11, a ring-shaped mirror is preferably used as the light separation section 18 as seen from FIG. 4. If a ring-shaped mirror is used, then light at a central portion passes by 100% to the light detector 14, and consequently, the light detection accuracy on the light detector 14 is improved. Further, since light at the ring portion is separated with certainty by the image confirmation section 16, the amount of light sufficient for position adjustment of the flow channel 11 can be assured sufficiently.

More particularly, for example, position adjustment can be carried out while the position of the flow channel 11 is monitored based on light separated to the image confirmation section 16 at the ring portion of the ring-shaped mirror. Simultaneously, since light at the central portion of the ring-shaped mirror passes by 100% to the light detector 14, the fluorescent light capturing efficiency from the specimen circulated in the flow channel 11 can be improved.

<2. Wavelength Calibration Method>

Figure 5:
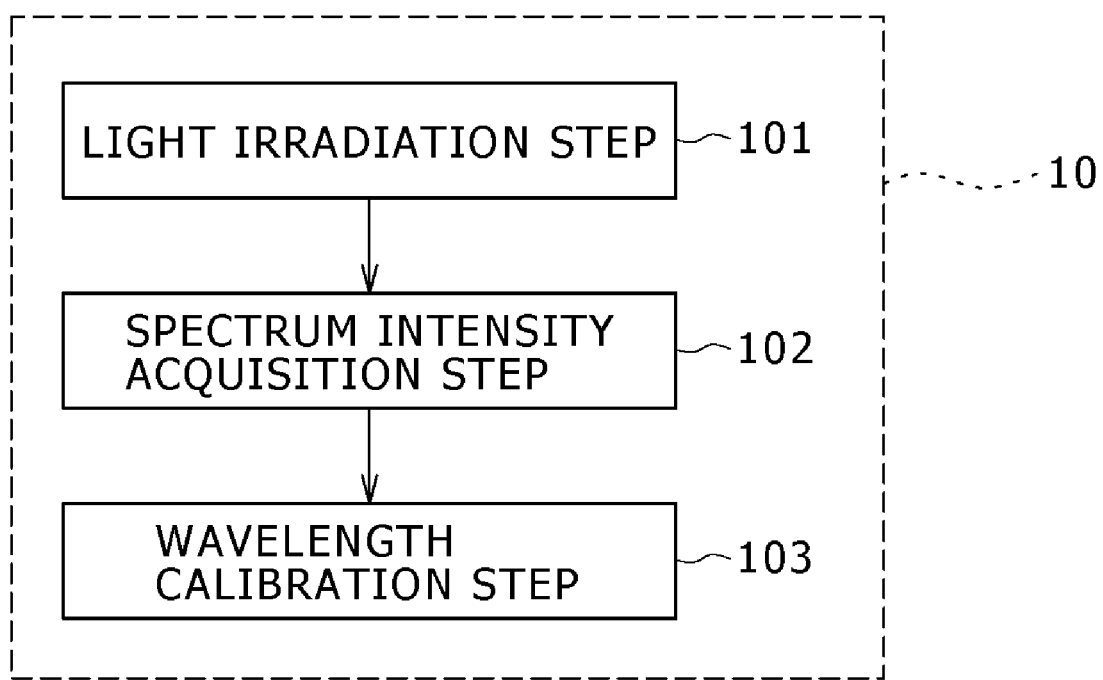
FIG. 5 is a flow chart of a wavelength calibration method according to an embodiment.

FIG. 5 is a flow chart illustrating a wavelength calibration method 10 according to an embodiment.

Referring to FIG. 5, the wavelength calibration method 10 roughly includes a light irradiation step 101, a spectrum intensity acquisition step 102 and a wavelength calibration step 103. The individual steps are described in detail below.

2-1. Light Irradiation Step 101

At the light irradiation step 101, LED light is irradiated upon the flow channel 11.

Although the type of the LED light used in the wavelength calibration method 10 is not limited particularly, preferably LED light of a spectrum intensity distribution having a spectrum width of 100 nm or more is used. This is because, if LED light having a great spectrum width of 100 nm or more is used, then optical axis adjustment after spectralization is carried out by the light detector 14 can be carried out easily at the spectrum intensity acquisition step 102. One of LED lights of a spectrum intensity distribution having a spectrum width of 100 nm or more is white-light LED light.

Preferably, an LED having a known spectrum intensity distribution is used. This is because, where an LED having a known spectrum intensity distribution is used, wavelength calibration can be carried out readily at the wavelength calibration step 103 hereinafter described.

According to the wavelength calibration method 10, since an LED is used, there is no necessity to use the condenser lens. Further, since the LED generates a comparatively small amount of heat, there is no necessity to take a countermeasure for heat radiation.

Further, since the LED is used, an image confirmation step 108 and a position adjustment step 109 of the optical measuring method 100 hereinafter described can be carried out over a wide visual field.

In addition, since the spectrum of the LED indicates not a bright line spectrum but a broad distribution, even if the resolution of the light detector 14 used in the optical measuring method 100 hereinafter described is low, a spectrum shift by a very small amount of optical axis adjustment can be detected and wavelength calibration of the light detector 14 can be carried out.

2-2. Spectrum Intensity Acquisition Step 102

At the spectrum intensity acquisition step 102, the spectrum intensity of light generated through the flow channel 11 at the light irradiation step 101 is acquired.

At the spectrum intensity acquisition step 102, the acquisition method is not limited particularly only if the spectrum intensity of light can be detected, and known methods can be selectively used freely. For example, the fluorimetry, scattered light measurement method, transmission light measurement method, reflection light measurement method, diffraction light measurement method, ultraviolet spectrometry, infrared spectrometry, Raman spectroscopy, FRET measurement method, FISH measurement method, various other spectrum measurement method, and a multicolor detection method by which a plurality of coloring matters can be detected can be freely adopted solely or in combination.

2-3. Wavelength Calibration Step 103

At the wavelength calibration step 103, wavelength calibration of the light detector 14 is carried out based on the spectrum intensity distribution acquired at the spectrum intensity acquisition step 102.

At the wavelength calibration step 103, the method therefor is not limited particularly only if wavelength calibration of the light detector 14 can be carried out. As an example, a method can be adopted wherein the spectrum intensity distribution (refer to in FIG. 3B) acquired at the spectrum intensity acquisition step 102 and the spectrum intensity distribution (refer to in FIG. 3A), determined in advance, of an LED same as that used at the light irradiation step 101 and are compared with each other to carry out wavelength calibration of the light detector 14.

<3. Optical Measuring Method>

Figure 6:
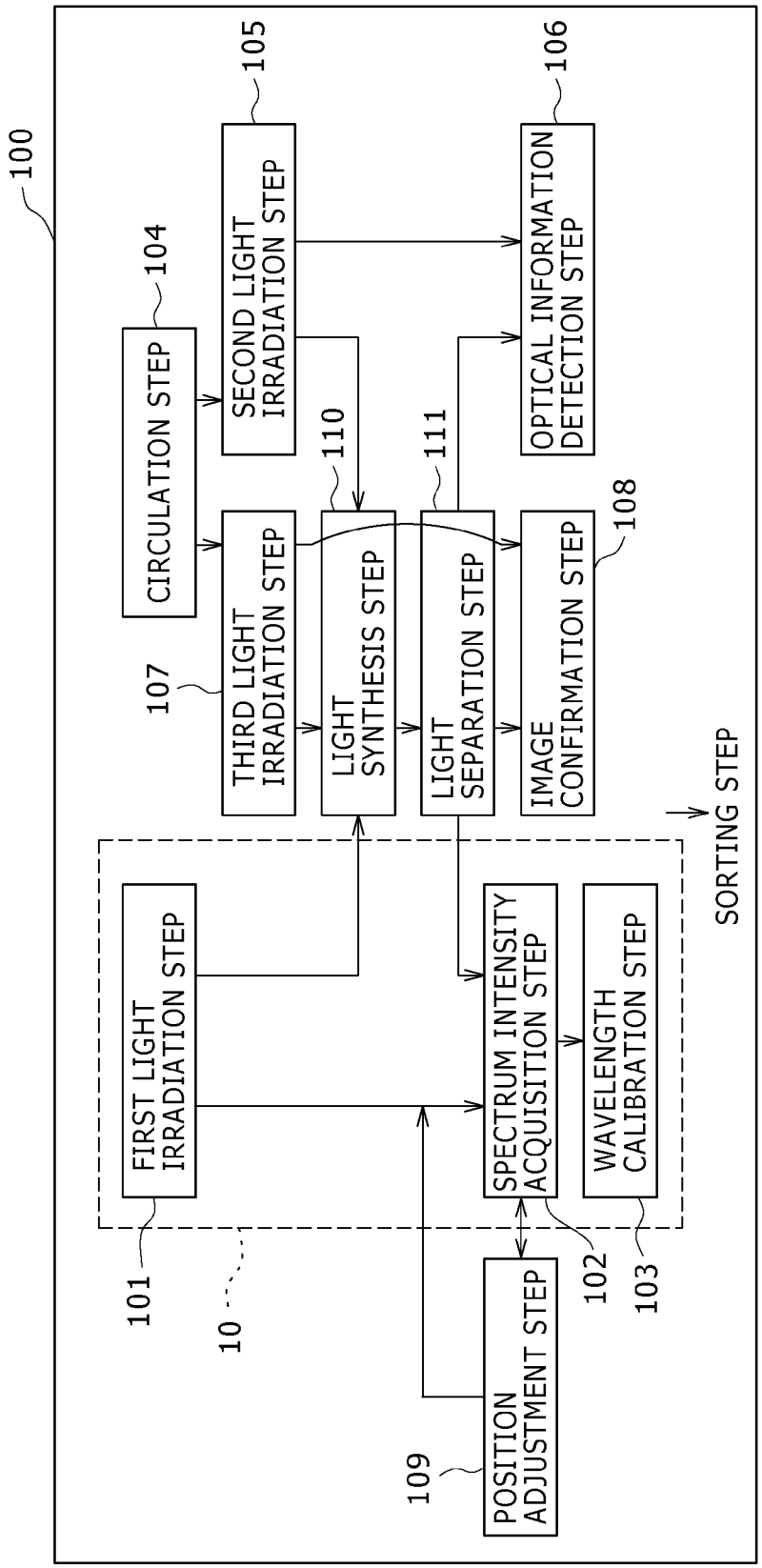
FIG. 6 is a flow chart of an optical measuring method according to an embodiment.

FIG. 6 is a flow chart of the optical measuring method 100.

Referring to FIG. 6, the optical measuring method 100 roughly includes a first light irradiation step 101, a spectrum intensity acquisition step 102, a wavelength calibration step 103, a circulation step 104, a second light irradiation step 105, and an optical information detection step 106. Further, as occasion demands, the optical measuring method 100 additionally includes a third light irradiation step 107, an image confirmation step 108, a position adjustment step 109, a light synthesis step 110 and a light separation step 111. In the following, the individual steps are described in detail. It is to be noted that the first light irradiation step 101, spectrum intensity acquisition step 102 and wavelength calibration step 103 correspond to the first light irradiation step 101, spectrum intensity acquisition step 102 and wavelength calibration step 103 described hereinabove of the wavelength calibration method 10 described hereinabove, respectively, and therefore, description of the steps mentioned is omitted herein to avoid redundancy.

3-1. Circulation Step 104

At the circulation step 104, the specimen S of an object of measurement is circulated into the flow channel 11.

Although the circulation method of the specimen S into the flow channel 11 is not limited particularly, for example, a method wherein the specimen S is transported while being sandwiched by a fluid medium which accelerates rectification, that is, by sheath flows. If the specimen S is transported in this manner, then laminar flows of a sample flow containing the specimen S can be formed more preferably. If the fluid medium has a function of accelerating rectification of the sample flow containing the specimen S, then although the type of the fluid medium is not limited particularly, for example, where the specimen S is cells, physiological salt solution or the like can be used.

Preferably, the specimen S is modified with a marker substance such as a fluorescent substance such as a fluorescent dye, a radioactive substance, an intercalator, or micro beads so that optical information can be detected at the optical information detection step 106 hereinafter described. For example, where a fluorescent dye is used, the type of the same is not limited particularly, and any known fluorescent dye can be used. For example, Cascade Blue, Pacific Blue, Fluorescein isothiocyanate (FITC), Phycoerythrin (PE), Propidium iodide (PI), Texas red (TR), Peridinin chlorophyll protein (PerCP), Allophycocyanin (APC), 4',6-Diamidino-2-phenylindole (DAPI), Cy3, Cy5, Cy7 and so forth can be freely used solely or in combination.

It is to be noted that, where the specimen S itself emits light like fluorescent protein, there is no necessity to modify the specimen S with a marker substance. Further, if a substance which can vary the fluorescent light color or the like of the substance by a principle like the principle of FRET by causing an interaction between substances to proceed in the flow channel 11 is used as the specimen S, there is no necessity to modify the specimen S with a marker substance.

3-2. Second Light Irradiation Step 105

At the second light irradiation step 105, light is irradiated upon the specimen S circulated in the flow channel 11. The order in which the second light irradiation step 105 is carried out is not limited particularly only if it is carried out later than the circulation step 104, and it may be carried out, for example, simultaneously with the first light irradiation step 101.

Although the type of the light to be irradiated at the second light irradiation step 105 is not limited particularly, in order for fluorescent light or scattered light to be generated with certainty from the specimen S, the light preferably is fixed in the light direction, wavelength and light intensity. As an example, a laser or LED can be used. Where a laser is used, although the type thereof is not limited particularly, an argon ion (Ar) laser, a helium-neon (He—Ne) laser, a dye laser, a krypton (Kr) laser and so forth may be freely used solely or in combination.

3-3. Optical Information Detection Step 106

At the optical information detection step 106, optical information emitted from the specimen S circulated in the flow channel 11 when light is irradiated at the second light irradiation step 105 is detected using the light detector 14. The order in which the optical information detection step 106 is carried out is not limited particularly only if it is carried out later than the second light irradiation step 105. However, preferably the optical information detection step 106 is carried out simultaneously with or after the wavelength calibration step 103. This is because the accuracy in detection of optical information from the specimen S is improved.

At the optical information detection step 106, the acquisition method is not limited particularly only if optical information from the specimen S can be detected, but known methods can be freely selected and used. For example, one, two or more of a fluorimetry, a scattered light measuring method, a transmission light measuring method, a reflection light measuring method, a diffraction light measuring method, an ultraviolet spectroscopy, a Raman spectrophotometry, an FRET measuring instrument, a FISH measuring instrument, various other spectrum measuring methods, a method which uses a multicolor detection method or the like which can detect a plurality of coloring matters and so forth can be freely used solely or in combination.

3-4. Third Light Irradiation Step 107

At the third light irradiation step 107, LED light is irradiated upon the flow channel 11 in which the specimen S is circulated.

The type of the LED used for irradiation at the third light irradiation step 107 is not limited particularly, and known LEDs can be freely selected and used. For example, if the LED used at the first light irradiation step 101 is used as it is, then this is convenient because there is no necessity to prepare a predetermined LED light sources.

It is to be noted that the third light irradiation step 107 may be carried out, for example, simultaneously with or before or after the second light irradiation step 105 as seen in FIG. 6 or may be carried out simultaneously with or before or after the optical information detection step 106 only if it is carried out later than the circulation step 104. Further, where the first light irradiation step 101 is carried out after the circulation step 104 is carried out, it is possible for the first light irradiation step 101 to play the role of the third light irradiation step 107 simultaneously.

3-5. Image Confirmation Step 108

At the image confirmation step 108, image confirmation in the flow channel 11 is carried out based on optical information generated through the flow channel 11 upon irradiation of LED light at the third light irradiation step 107.

At the image confirmation step 108, the confirmation method is not limited particularly only if image confirmation in the flow channel 11 can be carried out, and known methods can be freely selected and used. For example, a confirmation method which uses an area image pickup element such as a charge coupled device (CCD) element, a complementary metal oxide semiconductor (CMOS) device or the like can be used as the confirmation method.

Although the particular image confirmation method at the image confirmation step 108 is not limited particularly, as an example, a method is used wherein flashlight irradiation of LED light is carried out in synchronism with the circulation of the specimen S at the third light irradiation step 107 and the state of the specimen S such as the position, speed, shape or color is confirmed from an image based on optical information emitted from the specimen S upon the flashlight irradiation.

It is to be noted that the image confirmation step 108 may be carried out, for example, simultaneously with or before or after the second light irradiation step 105 or may be carried out simultaneously with or before or after the optical information detection step 106 only if it is carried out later than the third light irradiation step 107.

3-6. Position Adjustment Step 109

At the position adjustment step 109, position adjustment of the light detector 14 or the wavelength calibration section 15, which carries out image confirmation, is carried out based on optical information generated through the flow channel 11 when the first light irradiation step 101 and/or the third light irradiation step 107 is carried out.

More particularly, position adjustment and so forth of the light detector 14, the image confirmation section 16, and the second light source 13 and condensing lens a2 which carry out the second light irradiation step 105 with respect to the flow channel 11 are carried out based on optical information generated through the flow channel 11 upon irradiation of LED light toward the flow channel 11 at the first light irradiation step 101 and/or the third light irradiation step 107.

It is to be noted that, although the order in which the position adjustment step 109 is carried out is not limited particularly only if it is carried out later than the first light irradiation step 101 and/or the third light irradiation step 107, preferably the position adjustment step 109 is carried out, for example, simultaneously with or before or after the spectrum intensity acquisition step 102 as seen in FIG. 6. This is because, if the position adjustment step 109 is carried out later than the spectrum intensity acquisition step 102, then there is the possibility that the spectrum intensity obtained may be varied by the change of the position of the light detector 14 or the image confirmation section 16.

3-7. Sorting Step

A sorting step may be carried out later than the optical information detection step 106 and/or the image confirmation step 108 although this is not essentially required in the present application. At the sorting step, sorting of the specimen S is carried out based on optical information of the specimen S obtained at the optical information detection step 106 and/or the image confirmation step 108.

As a particular example, though not shown, flow channels for sorting are formed on the downstream of the flow channel 11, and the specimen S can be sorted using a deflection plate D or the like into the flow channels based on information of the size, form, internal structure and so forth of the specimen S obtained at the optical information detection step 106 and/or the image confirmation step 108.

3-8. Light Synthesis Step 110

At the light synthesis step 110, light emitted at the first light irradiation step 101 and/or the third light irradiation step 107 and light emitted at the second light irradiation step 105 are synthesized. Although the light synthesis step 110 is not essentially required for the optical measuring method 100, where the light synthesis step 110 is carried out, the following advantage can be anticipated.

Since the optical measuring method 100 includes at least two steps of irradiating light (first light irradiation step 101, second light irradiation step 105 and third light irradiation step 107), if the steps are carried out simultaneously to irradiate light, then at least one of the light beams is irradiated in an oblique direction upon the flow channel 11. If light is irradiated in an oblique direction upon the flow channel 11, then the scattering or reflection may occur, which may possibly have an influence on spectrum intensity detection of light or image detection. Therefore, it is a possible idea to synthesize the beams of light generated at the individual steps such that a resulting light beam is irradiated in a perpendicular direction upon the flow channel 11.

However, where a light source which emits light of a bright line spectrum and an excitation laser light source are used as in the related optical measurement, that one of bright line spectrum light wavelengths which overlaps with the wavelength of the excitation light cannot be used for the light synthesis, resulting in possibility that the utilization efficient of the light amount may drop.

On the other hand, in the optical measuring method 100, since an LED is used at the first light irradiation step 101 and the third light irradiation step 107, synthesis with the excitation light such as laser light is possible, and the influence of scattering or reflection of light upon spectrum intensity detection or image detection of light can be reduced. As a result, effective optical measurement with a high degree of accuracy can be anticipated.

Further, where LED light emitted at the third light irradiation step 107 and excitation light generated at the second light irradiation step 105 are synthesized and the synthesized light is irradiated in a perpendicular direction upon the flow channel 11, this gives rise to an advantage that, in image confirmation at the image confirmation step 108, the visual field of the monitor image becomes bright and the visual observability is improved.

Further, where the wavelength of the LED light generated at the first light irradiation step 101 and the third light irradiation step 107 is set sufficiently longer than the wavelength of excitation light generated at the second light irradiation step 105, the two wavelengths can be synthesized efficiently at the light synthesis step 110. As a result, also an advantage that the utilization efficiency of both of the LED light amount and the excitation light mount is enhanced is achieved.

The particular method at the light synthesis step 110 in the optical measuring method 100 is not limited particularly only if light emitted at the first light irradiation step 101 and/or the third light irradiation step 107 and light emitted at the second light irradiation step 105 can be synthesized, and known methods can be freely selected and used. For example, a dichroic mirror (DCM) or a beam splitter may be used for the light synthesis.

3-9. Light Separation Step 111

At the light separation step 111, light transmitted through the flow channel 11 is separated into light to the light detector 14 and light to the image confirmation section 16. It is necessary to separate light formed by synthesis of light emitted at the first light irradiation step 101 and/or the third light irradiation step 107 and light emitted at the second light irradiation step 105 at the light synthesis step 110 and transmitted through the same location of the flow channel 11 into light to the light detector 14 and light to the image confirmation section 16.

The particular method at the light separation step 111 in the optical measuring method 100 is not limited particularly only if light transmitted through the flow channel 11 can be separated into light to the light detector 14 and light to the image confirmation section 16, and known methods can be freely selected and used. For example, a method which uses a beam splitter or a ring-shaped mirror can be used.

Where a beam splitter is used, for example, if AR coating (Anti Reflection Coating) is applied only to one face, then light of a predetermined amount can be separated into light to the light detector 14 and light to the image confirmation section 16. In the optical measuring method 100, if the ratio of the light separation is set to 3 to 5% to the image confirmation section 16, then the light can be used sufficiently for image confirmation of the arrangement of the flow channel 11 or the manner in the flow channel 11.

Where the image confirmation step 108 is carried out for position adjustment of the flow channel 11, a ring-shaped mirror is preferably used to carry out the light separation step 111. If a ring-shaped mirror is used, then light at a central portion passes by 100% to the light detector 14, and consequently, the light detection accuracy on the light detector 14 is improved. Further, since light at the ring portion is separated with certainty to the image confirmation section 16, the amount of light sufficient for position adjustment of the flow channel 11 can be assured sufficiently.

More particularly, for example, position adjustment can be carried out while the position of the flow channel 11 is monitored based on light separated to the image confirmation section 16 at the ring portion of the ring-shaped mirror. Simultaneously, since light at the central portion of the ring-shaped mirror passes by 100% to the light detector 14, the fluorescent light capturing efficiency from the specimen circulated in the flow channel 11 can be improved.

3-10. Flow of the Optical Measuring Method 100

An example of a particular flow of the optical measuring method 100 described above is described with reference to FIG. 1 in which the optical measuring instrument 1 is shown.

First, LED light irradiation upon the flow channel 11 formed on the substrate T is carried out using the first light source 12 at the first light irradiation step 101 to adjust the position of the image confirmation section 16 so that the flow channel 11 is projected to the image confirmation section 16. The positional relationship between the flow channel 11 and the image confirmation section 16 can be adjusted in this manner at the position adjustment step 109.

Then, in a state wherein the spatial filter d1 is removed, the LED light transmitted through the flow channel 11 is projected to the light detector 14. At this time, if a paper sheet or the like is placed on the surface of the light detector 14, then the state wherein the spectralized LED light is projected can be observed readily. Although an image of the flow channel 11 is projected simultaneously with the LED light, the position of the light detector 14 is adjusted so that the image is disposed at the center of the light detector 14 and can be observed definitely. The positional relationship between the flow channel 11 and the light detector 14 can be adjusted in this manner at the position adjustment step 109.

Then, in addition to the LED light, for example, a laser beam is irradiated from the second light source 13 upon the flow channel 11. At this time, part of the laser beam transmitted through the flow channel 11 is reflected by a beam splitter b2 and most of the reflected light is cut by a band cut filter c1. However, very small part of the reflected light is transmitted through the band cut filter c1 and comes to the image confirmation section 16. The position of the laser and/or the position of the condensing lens a2 are adjusted while the image of the image confirmation section 16 is observed so that a spot of the laser coming to the image confirmation section 16 is irradiated in a desired spot size upon a desired position of the flow channel 11. The positional relationship between the second light source 13 and the flow channel 11 can be adjusted in this manner at the position adjustment step 109. Although the arrangement regarding at which position of the flow channel 11 light is irradiated on the flow channel 11 on the screen of the image confirmation section 16 cannot be confirmed only through irradiation from the second light source 13, if LED light irradiation is carried out using the first light source 12, then the positional relationship between the flow channel 11 and the light irradiation spot can be confirmed readily in this manner.

Then, the spatial filter d1 which has been removed is mounted back, and the first light source 12 is turned off. In this state, the specimen S modified, for example, with a fluorescent dye is circulated in the flow channel 11. Consequently, part of fluorescent light excited by a laser beam L irradiated from the second light source 13 comes to and is spectralized by a diffraction grating e1 and then projected on the light detector 14. The position of the spatial filter d1 is adjusted so that the projected fluorescence spectrum is projected to the inside of an effective area of the light detector 14. The positional relationship between the laser irradiation position on the flow channel 11 and the spatial filter d1 can be adjusted in this manner.

Then, the specimen S in the flow channel 11 is discharged once, and the second light source 13 is turned off and the first light source 12 is turned on to irradiate LED light upon the flow channel 11 at the first light irradiation step 101. Part of the LED light transmitted through the flow channel 11 is projected in a spectralized state to the light detector 14. Then, the paper sheet placed on the light detector 14 is removed and the spectrum intensity distribution is acquired by the light detector 14 at the spectrum intensity acquisition step 102. Then, the detected spectrum distribution is compared with the LED light spectrum distribution determined in advance to calibrate the detection wavelength of the light detector 14 at the wavelength calibration step 103.

Then, the first light source 12 is turned off and the specimen S modified, for example, with a fluorescent dye is circulated into the flow channel 11 at the circulation step 104. The second light source 13 is used to irradiate, for example, the laser beam L on the specimen S circulated in the flow channel 11 at the second light irradiation step S105. Consequently, part of fluorescent light excited by the laser beam L comes to and is spectralized by the diffraction grating e1 and can be detected by the light detector 14 at the optical information detection step 106.

On the other hand, the first light source 12 is used to irradiate LED flashlight upon the flow channel 11 in synchronism with the circulation of the specimen S at the third light irradiation step 107. At this time, where the irradiation of the laser beam L at the second light irradiation step 105 and the flashlight irradiation of the LED light at the third light irradiation step 107 are carried out simultaneously, also it is possible to use a beam splitter or a DCM to synthesize the laser beam L and the LED light at the light synthesis step 110. In this instance, the synthesized light incident to the flow channel 11, for example, the light going out from the flow channel 11, is captured by a condensing lens a3, and the light separation section 18 such as a beam splitter or a ring-shaped mirror coated on only one face thereof is used to separate a predetermined amount of light to the image confirmation section 16 at the light separation step 111.

Then, by confirming optical information generated through the flow channel 11 upon the LED flashlight irradiation by the image confirmation section 16, the state of the specimen S such as the position, speed, shape or color can be confirmed based on an image at the image confirmation step 108. It is to be noted that, at this time, as a result of the LED flashlight irradiation, the spectrum of the LED light is sometimes superposed on the value detected at the optical information detection step 106, and therefore, attention should be paid.

If, after the series of steps described above, it is tried to exchange the substrate T to carry out subsequent measurement, then if the LED light is irradiated on the flow channel 11 formed on the new substrate T using the first light source 12 and the adjustment is carried out so that the flow channel 11 comes to the predetermined position on the screen of the image confirmation section 16, then optical measurement can be carried out again with a high degree of reproducibility. In this manner, since the position of the second light source 13, light detector 14 and so forth is in a state adjusted relative to the image confirmation section 16, the adjustment can be carried out readily only by confirmation on the screen of the image confirmation section 16.

WORKING EXAMPLE 1

In a working example 1, a white-light LED was used to carry out wavelength calibration of a light detector.

First, the spectrum of light from the white-light LED was measured using a popular spectrophotometer. As a result, a wavelength, a half value width (wavelength at which the intensity assumes a half value) and so forth of peaks existing in a spectrum distribution were obtained.

Figure 7:
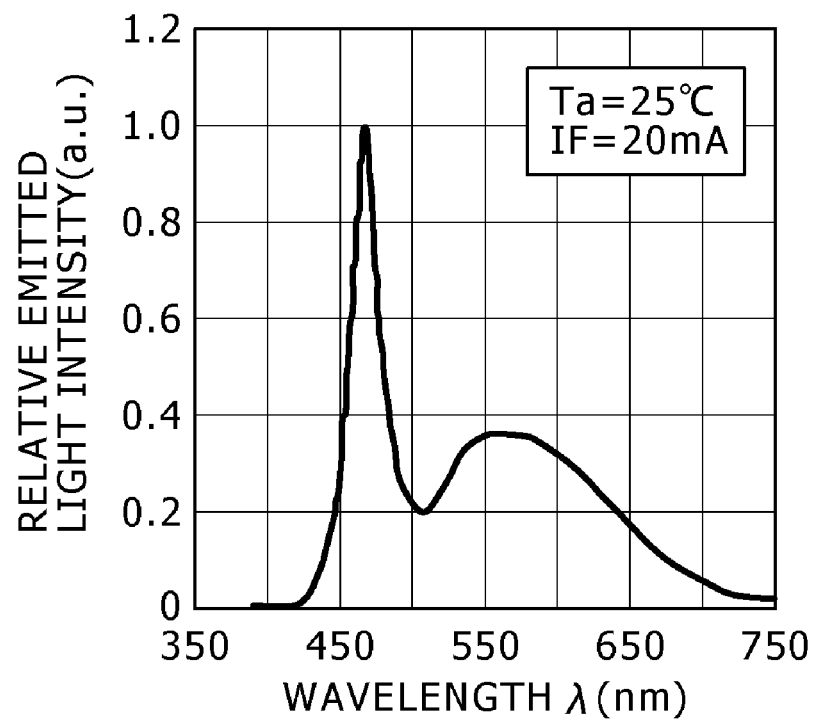
FIG. 7 is a graph illustrating a result of measurement of the spectrum of light emitted from a white-light LED using a popular spectrophotometer in a working example according to an embodiment.

A result of the measurement is illustrated in FIG. 7. As seen in FIG. 7, the first peak wavelength was 470 nm, and the second peak wavelength was 560 nm. Further, as the value at which the half value intensity is exhibited, such values as 455 nm and 480 nm on the opposite sides of the first peak and 650 nm on the long wavelength side of the second peak were obtained. It is to be noted that, since the half value wavelength on the shorter wavelength side of the second peak was lifted by the first peak, no value was obtained.

Then, in the optical measuring instrument shown in FIG. 1, a light source formed from a white-light LED was installed as the first light source to carry out spectrum intensity distribution measurement on a multichannel PMT.

Figure 8:
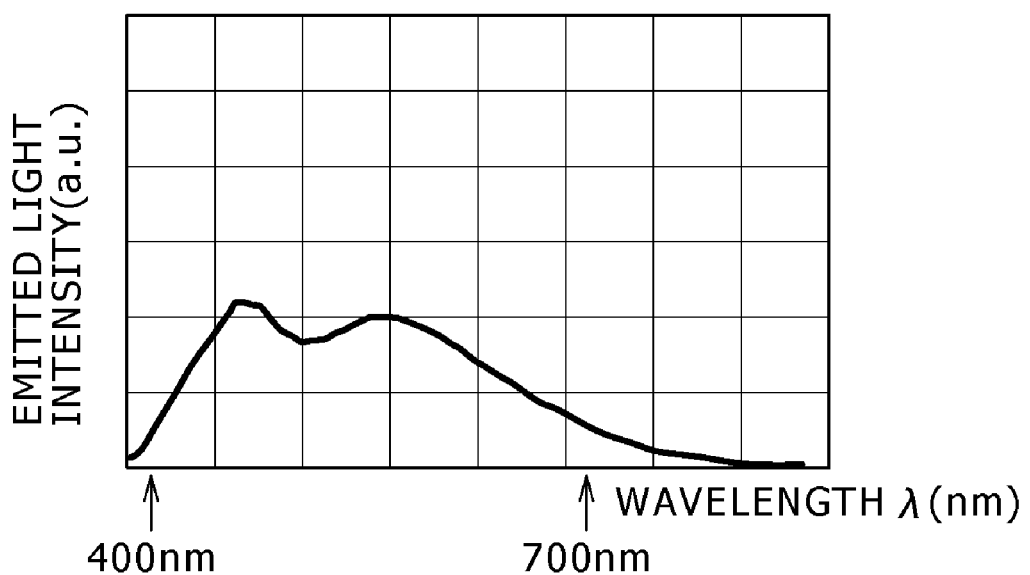
FIG. 8 is a graph illustrating a result of measurement of the spectrum of light emitted from the white-light LED using an optical measuring instrument in the working example according to an embodiment.

A result of the measurement is illustrated in FIG. 8. The measurement result was fitted to the spectrum intensity distribution illustrated in FIG. 7 to carry out wavelength calibration of the multichannel PMT. More particularly, the two fitting wavelengths of 400 nm and 700 nm are used to carry out wavelength calibration of the multichannel PMT.

It is to be noted that, while, in the present embodiment, the fitting wavelengths at two points are used to carry out wavelength calibration, in order to further raise the accuracy, also it is possible to carry out fitting with a plurality of wavelengths. Further, also where the light detector for detecting the spectrum intensity has nonlinearity, calibration can be carried out more accurately by carrying out fitting by polynomial approximation.

WORKING EXAMPLE 2

In a working example 2, the optical measuring instrument 1 was used to carry out light synthesis and light separation by the optical measuring method to carry out image confirmation. In the present working example, as an example of the LED light to be emitted from the first light source, LED light in a wavelength band having a half value width of approximately 20 nm with respect to the center of the wavelength of 630 nm was used. Meanwhile, as an example of light to be emitted from the second light source, excitation laser light of a wavelength of 488 nm was used.

First, the LED light emitted from the first light source 12 and the excitation laser light emitted from the second light source 13 were synthesized using a DCM, that is, the light synthesis section 17. The synthesized light was irradiated upon the flow channel 11 through the condensing lens a2. Thereupon, the LED light used for the synthesis was successfully irradiated upon the flow channel 11 sufficiently.

Then, the light emitted from the flow channel 11 was captured by the condensing lens a3, and a beam splitter coated with an AR coating only on one face thereof was used to separate an amount of light of approximately 4% to the CCD side, that is, to the image confirmation section 16 side. The separated light flux was irradiated upon the CCD, that is, upon the image confirmation section 16, to form an image thereby to monitor the arrangement of the flow channel 11 or the manner in the inside of the flow channel 11.

Then, a ring-shaped mirror, that is, the light separation section 18, was arranged in place of the beam splitter described above such that a ring portion of light emitted from the flow channel 11 was separated to the CCD, that is, to the image confirmation section 16 and a central portion of the light was separated to the light detector 14. Although the image on the CCD, that is, on the image confirmation section 16, had no central portion, the position adjustment of the flow channel 11 was carried out successfully without any problem. Further, since the light at the central portion passed by 100% to the light detector 14 side, the fluorescent light acquisition efficiency of the light detector 14 exhibited significant enhancement.

From the result of the working example 2. it was found that, by setting the wavelength of light to be emitted from the first light source 12 longer than the wavelength of light to be emitted from the second light source 13, the light synthesis section 17 was able to carry out the light synthesis while maintaining a high efficiency. Also it was found that, as the amount of light to be separated to the image confirmation section 16, approximately 4% was sufficient for image confirmation, and the light amount of loss to the light detector 14 side was very small.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An optical measuring instrument, comprising:
   a flow channel for allowing a specimen to be circulated therein, said flow channel including a top surface and a bottom surface;
   a first light source including a light emitting diode for emitting light upon said top surface of said flow channel to be used for optical adjustment and/or image confirmation in said flow channel;
   a second light source for irradiating light upon said top surface of said flow channel to irradiate light upon the specimen circulated in said flow channel; and
   a light detector for detecting the spectrum intensity of the light emitted from said first and second light sources;
   an image confirmation means for carrying out image conformation in said flow channel based on optical information generated through said flow channel by irradiating the light upon said flow channel using said first light source; and
   a light separation means for separating the light transmitted through said flow channel to light to said light detector and light to said image confirmation means.

2. The optical measuring instrument according to claim 1, further comprising wavelength calibration means for carrying out wavelength calibration of said light detector based on the spectrum intensity, detected by said light detector, of the light emitted from said first light source.

3. The optical measuring instrument according to claim 2, wherein said wavelength calibration means compares a spectrum intensity distribution, detected by said light detector, of the light emitted from said light source with a spectrum intensity distribution determined in advance of said light emitting diode to carry out the wavelength calibration of said light detector.

4. The optical measuring instrument according to claim 1, wherein said first light source carries out flashlight irradiation in synchronism with the circulation of the specimen, and said image confirmation means confirms the state of the specimen through an image based on the optical information generated from the specimen upon the flashlight irradiation.

5. The optical measuring instrument according to claim 1, further comprising light synthesis means for synthesizing the light emitted from said first light source and the light emitted from said second light source.

6. The optical measuring instrument according to claim 5, wherein said light synthesis means includes a dichroic mirror or a beam splitter.

7. The optical measuring instrument according to claim 1, wherein said light separation means includes a ring-shaped mirror.

8. The optical measuring instrument according to claim 1, wherein said light emitting diode exhibits a spectrum intensity distribution having a spectrum width of 100 nm or more.

* * * * *